United States Patent
Dong et al.

(10) Patent No.: US 8,621,689 B2
(45) Date of Patent: Jan. 7, 2014

(54) APPARATUS FOR DRIVING AND SUPPORTING CRADLE AND MR SYSTEM HAVING THE SAME

(75) Inventors: Yifei Dong, Beijing (CN); Xin Yang, Beijing (CN); Bing Luo, Beijing (CN); Tiexin Liu, Beijing (CN)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 251 days.

(21) Appl. No.: 13/174,185

(22) Filed: Jun. 30, 2011

(65) Prior Publication Data

US 2012/0000016 A1 Jan. 5, 2012

(30) Foreign Application Priority Data

Jun. 30, 2010 (CN) .......................... 2010 1 0226815

(51) Int. Cl.
*A61G 13/02* (2006.01)

(52) U.S. Cl.
USPC ........................................ 5/601; 5/600; 5/943

(58) Field of Classification Search
USPC ................................ 5/943, 600–601, 81.1 HS
See application file for complete search history.

(56) References Cited

U.S. PATENT DOCUMENTS

| | | | | |
|---|---|---|---|---|
| 6,615,428 | B1 * | 9/2003 | Pattee | 5/601 |
| 7,430,772 | B2 | 10/2008 | Van Es | |
| 2005/0204472 | A1 * | 9/2005 | Gagneur et al. | 5/601 |
| 2007/0143921 | A1 | 6/2007 | Hiyama | |

* cited by examiner

*Primary Examiner* — Fredrick Conley
(74) *Attorney, Agent, or Firm* — Armstrong Teasdale LLP

(57) ABSTRACT

An apparatus for driving and supporting cradle includes a table base and a cradle movable on the table base. The cradle includes an intermediate cradle moveable relative to the table base and an upper cradle moveable relative to the intermediate cradle. The table base is coupled to the intermediate cradle using a first rack and gear structure, and the intermediate cradle is coupled to the upper cradle using a second rack and gear structure.

16 Claims, 4 Drawing Sheets

APPARATUS FOR DRIVING AND SUPPORTING CRADLE AND MR SYSTEM HAVING THE SAME

CROSS REFERENCE TO RELATED APPLICATIONS

This application claims the benefit of Chinese Patent Application No. 201010226815.3 filed Jun. 30, 2010, which is hereby incorporated by reference in its entirety.

BACKGROUND OF THE INVENTION

The embodiments described herein relate to the field of medical imaging equipment, especially to a magnetic resonance (MR) system, and particularly to a mechanical structure for driving and supporting cradle.

As shown in FIG. 1, a MR system usually includes a table (1), a magnet (2) and a rear pedestal (3). The table (1) is movable in forward and reverse and can move up and down. A cradle (4) on the table can move relative to the table so as to carry a patient into the magnet bore. When a front part of the cradle passes through the magnet bore and moves out of the magnet bore, a bridge (5) supports the front part of the cradle. The rear pedestal includes a cradle supporting element (6) and a drive motor (7). The drive motor drives the cradle supporting element to provide support to the protruding cradle when the cradle passes though and protrudes from the magnet bore.

Such known structure has the following problems. Because the table must be movable and can move up and down, the whole cradle (front part and rear part) tightly fits within the magnet bore, and thus it is difficult to realize a longer scanning range. Besides, in an emergency (e.g. when the system is out of power), the cradle inserted into the magnet bore cannot be withdraw immediately. Instead, the cradle can only be pulled out of the magnet bore by an operator manually. Moreover, the rear pedestal requires a rather large room, and thus the MR system is required to be housed in a large scanning room. As such, a facility to perform operations, such as surgical procedure, while performing MR scanning may be difficult to obtain.

The rear pedestal mainly has two functions. First, the rear pedestal forms a support for the cradle moving into the magnet bore so as to reduce cradle sag. The read pedestal further drives the movement of the cradle. Therefore, a new structural for driving and supporting cradle is described below to remove the rear pedestal. The embodiments described herein are further configured to realize a longer scanning range and to ensure timely release of the cradle in case of emergencies.

U.S. Pat. No. 7,430,772 discloses a single-cradle driving and supporting mechanism realized with three toothed racks. However, the single-cradle limits the scanning range, the cost of the structure of three toothed racks is high, and the control precision thereof is low. Further, U.S. Pub. No. 2007/0143921 discloses a double-cradle driving and supporting structure realized with a double belt pulley. However, the table cannot move freely to ensure safety since the drive motor is located on the table base.

SUMMARY OF THE INVENTION

In one aspect, an apparatus for driving and supporting mechanism includes a table base and a cradle movable on the table base. The cradle includes two layers, and the table base is connected to an intermediate cradle through a rack and gear structure. The intermediate cradle is movable relative to the table base and connected to an upper cradle through a rack and gear structure. The upper cradle is movable relative to the intermediate cradle.

A rack is fixed on the upper cradle, and a first gear is fixed on the intermediate cradle. The rack on the upper cradle is engaged with the first gear on the intermediate cradle. When the intermediate cradle moves, the first gear rotates and drives the upper cradle to move by the rack. A second gear is fixed on the intermediate cradle, and a rack is fixed on the table base. The rack on the table base is engaged with the second gear on the intermediate cradle. The movement of the intermediate cradle drives the second gear to rotate and moves relative to the table base through the gear and rack connection.

The first and second gears on the intermediate cradle are located at the two sides of the intermediate cradle, respectively. The first and second gears each have a coaxial pulley, and the two pulleys are connected through a belt. The belt links the two pulleys, and the pulleys drive the two gears. The two racks-two gears structure drives the upper cradle and the intermediate cradle to move in the same direction.

The first and second gears have the same radius, and the two pulleys have the same number of teeth.

A handle is provided on the intermediate cradle and at the outer side opposite to the moving direction thereof.

A cradle supporting part separate from the bed is further included. When a part of the cradle moves out of the table base, the cradle supporting part supports the part of cradle.

The cradle supporting part includes a bridge and a cradle supporting layer. The cradle supporting layer moves on the bridge and provides support below the moving cradle.

A motor is provided at a side of bridge, and a gearing is further included. The motor is connected to the gearing, which is in turn connected to the cradle supporting layer.

The gearing includes pulleys and a belt. The motor drives the pulleys and the belt, which drives the cradle supporting layer to move on the bridge.

A hook is provided on the outer side of the intermediate cradle in the same direction as the moving direction thereof. A hook is provided on the outer side of the side of the cradle supporting layer close to the cradle. When the cradle supporting layer moves to the side of the intermediate cradle, the hook on the outer side of the cradle supporting layer hooks on to the hook on the outer side of the intermediate cradle.

In another aspect, a magnetic resonance system includes a table and a magnet part. The table includes a table base and a cradle movable on the table. The cradle has two layers. The table base is connected to the intermediate cradle through a rack and gear structure, and the intermediate cradle can move relative to the table base. The intermediate cradle is connected to the upper cradle through a rack and gear structure, and the upper cradle can move relative to the intermediate cradle.

A rack is fixed on the upper cradle, and a first gear is fixed on the intermediate cradle. The rack on the upper cradle is engaged with the first gear on the intermediate cradle. When the intermediate cradle moves, the first gear rotates and drives the upper cradle to move by the rack. A second gear is fixed on the intermediate cradle, and a rack is fixed on the table base. The rack on the table is engaged with the second gear on the intermediate cradle, and the movement of the intermediate cradle drives the second gear to rotate and moves relative to the table base through the gear and rack connection.

The first and second gears on the intermediate cradle are located at the two sides of the intermediate cradle, respectively. The first and second gears each have a coaxial pulley, and the two pulleys are connected through a belt. The belt links the two pulleys, and the pulleys drive the two gears. The two racks-two gears structure drives the upper cradle and the intermediate cradle to move in the same direction.

The first and second gears have the same radius, and the two pulleys have the same number of teeth.

A handle is provided on the outer side of the intermediate cradle opposite to the moving direction thereof.

A cradle supporting part separate from the table is further included. When a part of the cradle moves out of the table, the cradle supporting part supports the part of cradle.

The cradle supporting part includes a bridge and a cradle supporting layer, wherein the cradle supporting layer can move on the bridge and provides support below the moving cradle.

A motor is provided at a side of the bridge beyond the influence range of the magnet bore. A gearing is further included, and the motor is connected to the gearing, which is in turn connected to the cradle supporting layer.

The gearing includes pulleys and a belt. The motor drives the pulleys and the belt, which drives the cradle supporting layer to move on the bridge.

A hook is provided on the outer side of the intermediate cradle in the same direction as the moving direction thereof. A hook is provided on the outer side of the side of the cradle supporting layer close to the cradle. When the cradle supporting layer moves to the side of the intermediate cradle, the hook on the outer side of the cradle supporting layer hooks on to the hook on the outer side of the intermediate cradle.

The embodiments described herein realize a longer scanning range by using double cradles, lowers the requirement on the space of a scan room, and facilitates a doctor to perform surgical procedures at the position usually occupied by the rear pedestal and thereby simplifies the system. The apparatus for driving and supporting cradle can ensure free movement of the table and reduce cradle sag during movement and ensure the safety in emergencies in the meanwhile.

DETAILED DESCRIPTION OF THE INVENTION

The present invention is further explained in detail below by embodiments of the present invention, but the present invention is not limited thereto.

The embodiments described herein provide a double-cradle structure. More specifically, a cradle supporting layer is added on the bridge for supporting an upper cradle extending into the magnet bore. A drive motor is located at a side of the bridge and a rear pedestal is omitted. The drive motor drives the cradle supporting layer to move using belt pulleys. The cradle supporting layer hooks onto the intermediate cradle by using a hook and drives the intermediate cradle to move. The intermediate cradle drives the upper cradle to be inserted into the magnet bore through the connection and driving between the intermediate cradle and the upper cradle.

Embodiments in accordance with the present invention are described in detail below in connection with the drawings, but the embodiments are not intended to limit the present invention, wherein the same component parts in different drawings are indicated with the same reference number.

Figure 1:
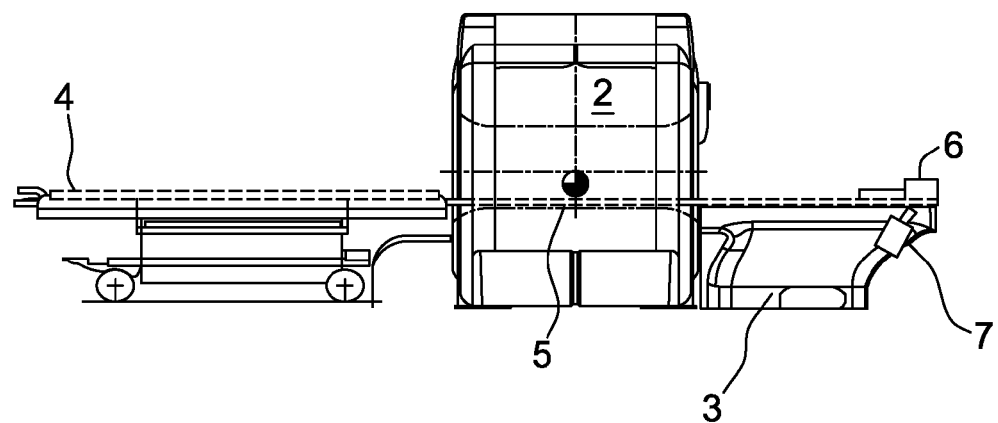
FIG. 1 shows a structural diagram of a known general MR system.
Figure 2:
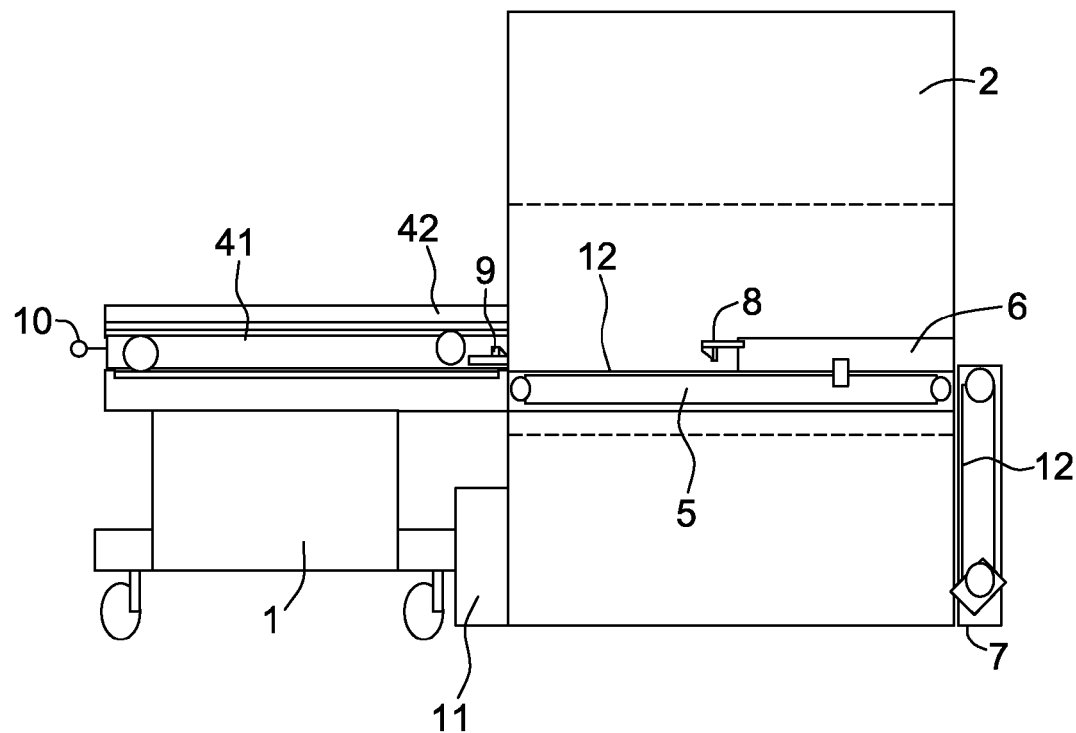
FIG. 2 shows a structural diagram of an exemplary MR system.

FIG. 2 shows the structural diagram of a MR system according to the present invention. As shown in FIG. 2, a MR system includes a table (1) and a magnet bore (2). The table contacts a connection part (11) when moving to a side of the magnet bore. Two layers of cradles are provided on the table base, namely, an intermediate cradle (41) and an upper cradle (42). A bridge (5) is provided in the magnet bore, and a cradle supporting layer (6) is positioned on the bridge. The rear pedestal is omitted from a first side of the magnet bore where a rear pedestal is positioned in a known MR system. A drive motor (7) is positioned immediately next to the bridge in the lower part of the first side and beyond the influence of the magnet bore. The motor drives the cradle supporting layer (6) to move using a gearing (12). The gearing includes pulleys and a belt. The cradle supporting layer couples to the hook (9) on the intermediate cradle (41) near the cradle supporting layer using a hook (8) near the side of the cradle. The coupling drives the intermediate cradle to move. Further, a handle (10) is included on the intermediate cradle. In emergencies, for example, a power-down of the system, the hooks between the intermediate cradle and the cradle supporting layer can be disconnected by simply manually pulling to release the cradle. With this structure, the drive motor is located at the side of the magnet bore immediately next to the bridge and beyond the influence of the magnet bore. As such, the table is movable freely without causing any safety problems due to the drive motor.

Figure 3:
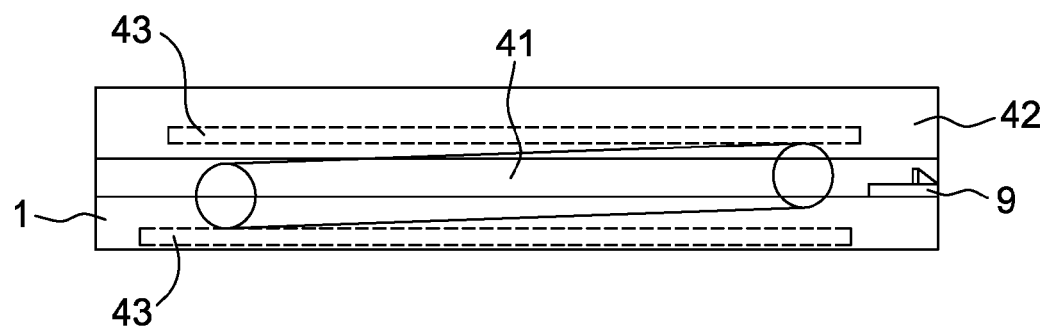
FIG. 3 is a side view of the structural diagram of the cradle part in accordance with the MR system shown in FIG. 2.
Figure 4:
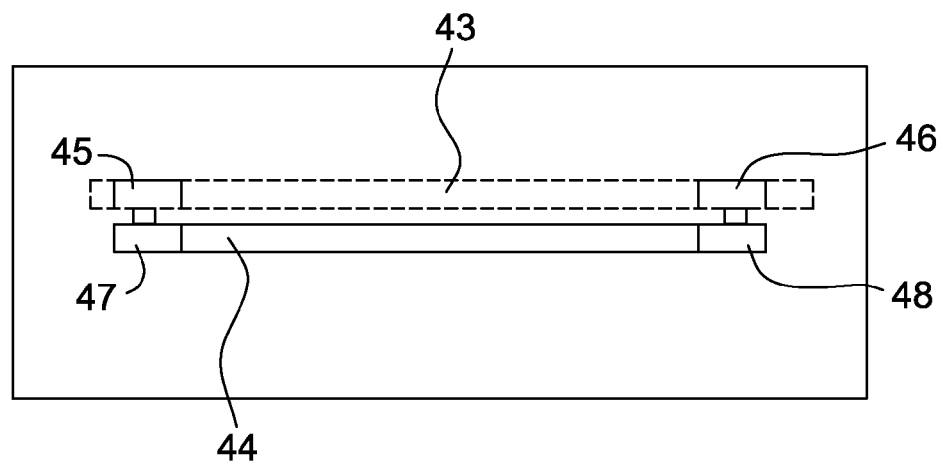
FIG. 4 is a top view of the structural diagram of the cradle part shown in FIG. 3.

FIGS. 3 and 4 show the structural diagram of the cradle part of the MR system. FIG. 3 is a side view and FIG. 4 is a top view. The two cradles are connected and driven through a two racks-two gears structure. The gears structure includes a gear (45) coupled to the intermediate cradle. When the cradle supporting layer drives the intermediate cradle to move into the magnet bore, the gear (45) rotates clockwise. Because the belt pulley (47) and the gear (45) are coaxial, the belt pulley (47) also rotates clockwise. Further, because the belt pulley (48) and the belt pulley (47) are connected through a belt, the belt pulley (48) also rotates clockwise. Moreover, because the gear (46) and the belt pulley (48) are coaxial, the gear (46) thus rotates clockwise. The gear (46) drives the rack (43) on the upper cradle, to move the upper cradle into the magnet bore.

Due to the two racks-two gears structure, the speed of the relative movement between the intermediate cradle and the upper cradle can be changed flexibly through adjusting the basic circle radius of gears (45) and (46) and the number of teeth of the pulleys (47) and (48). For example, if the radius of the gears (45) and (46) are the same and the numbers of teeth of the pulleys (47) and (48) are the same, then the moving speed of the upper cradle relative to the intermediate cradle is the same as the moving speed of the intermediate cradle relative to the table. Or, if the number of teeth of pulley (47)/the number of teeth of pulley (48)=n and the radius of gear (45)/the radius of gear (46)=1/n, the moving speed of the upper cradle relative to the intermediate cradle is the same as the moving speed of the intermediate cradle relative to the table base.

Figure 5:
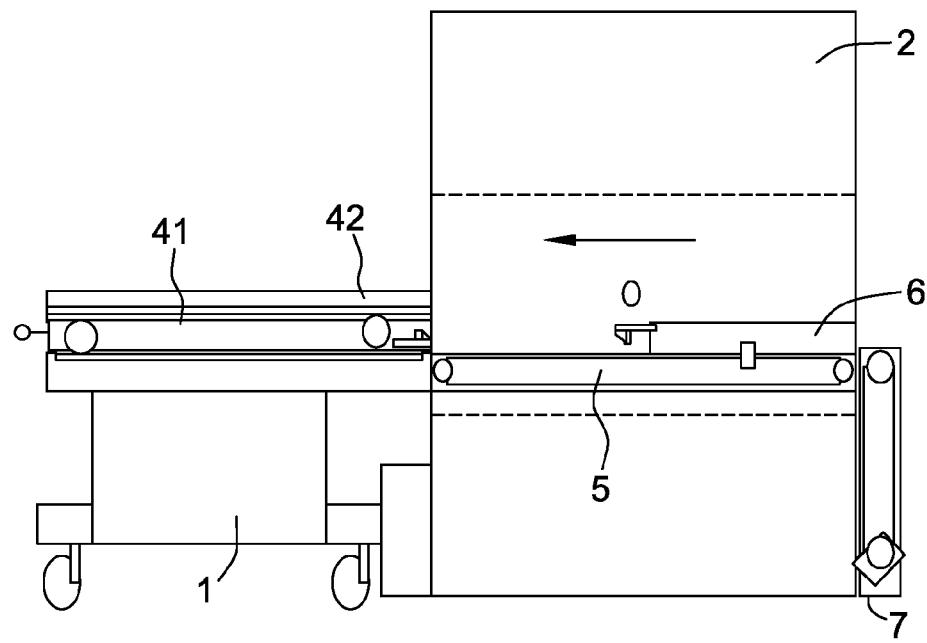
FIGS. 5, 6 and 7 shows the working mechanism diagrams of apparatus driving and supporting cradle that may be used with the MR system shown in FIG. 2.
Figure 6:
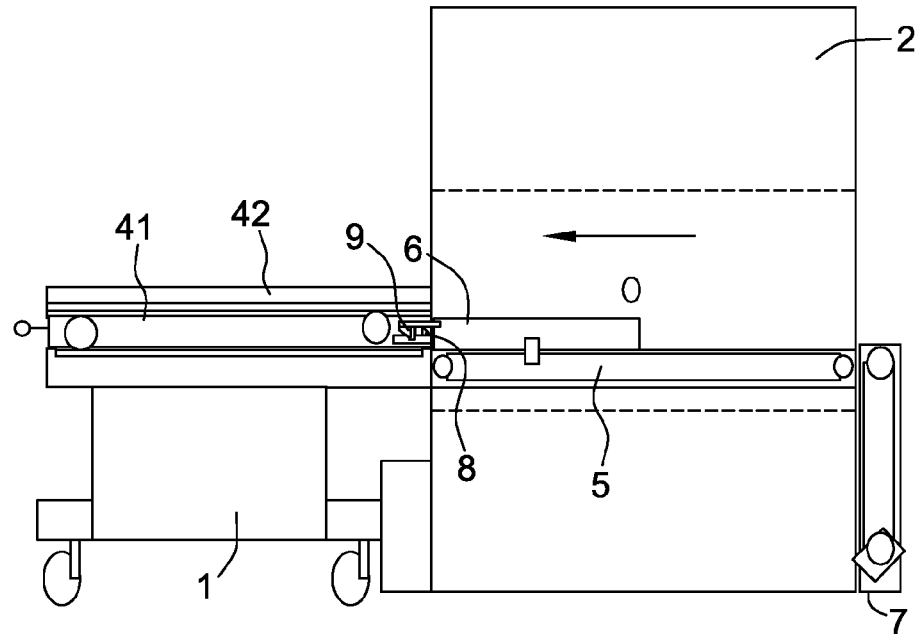
Figure 7:
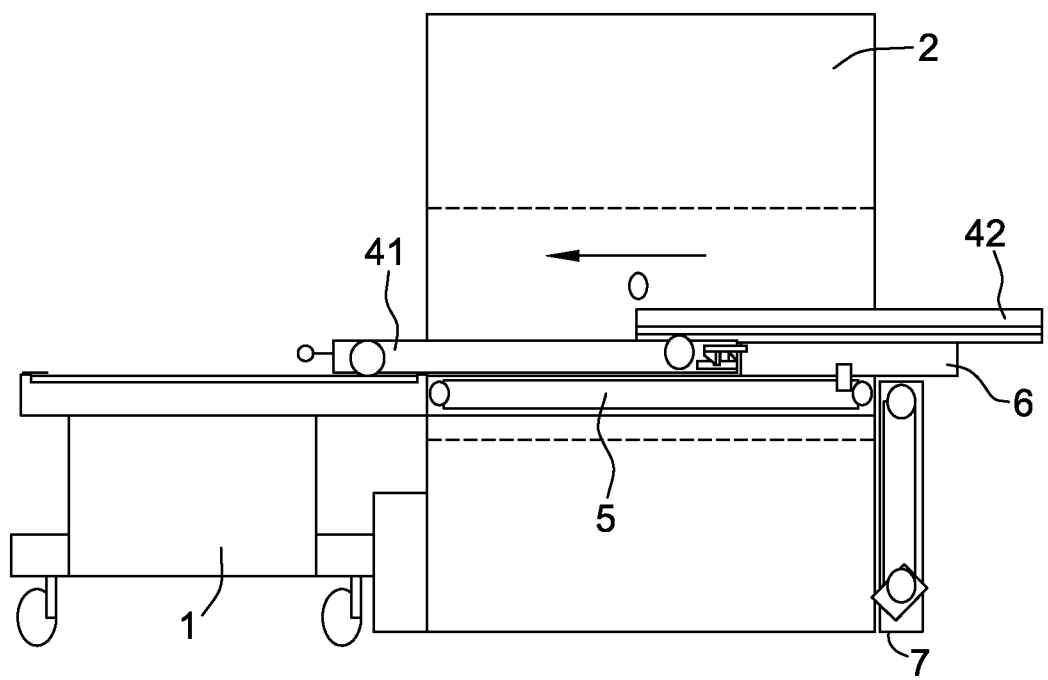

FIGS. 5, 6 and 7 show the working mechanism diagrams of the apparatus for driving and supporting the cradle. FIG. 5 shows an initial position in which the left side cradle is not positioned within the magnet bore and the cradle supporting layer (6) is positioned at an end of the magnet bore (2) opposing the cradle. FIG. 6 shows when the cradle is to be moved into the magnet bore. To move the cradle into the magnet bore, the motor (7) at the first side of the magnet bore drives the cradle supporting layer toward the cradle, and the cradle supporting layer couples to the intermediate cradle (41) using the hooks (8) and (9). FIG. 7 shows when the cradle supporting layer has driven the intermediate cradle to move into the magnet bore, and the intermediate cradle drives the upper cradle (42) to extends into the magnet bore. As such, the rack and gear connection and the movement between the intermediate cradle and the upper cradle achieves a longer scanning range.

The apparatus for driving and supporting cradle described herein can be applied to other imaging diagnostic apparatus in addition to a MR system, such as X-ray computed tomography (CT), positron emission tomography (PET) and X-ray imaging system, etc.

The above-described embodiments relate to an apparatus for driving and supporting cradle and a magnetic resonance system using the apparatus. More specifically, a double-cradle structure is used in the apparatus. Two cradles are coupled to each other and driven by a rack and gear structure. The apparatus further includes a cradle supporting part separate from a table, and a cradle supporting layer is coupled on the supporting bridge for supporting the protruding upper cradle. A drive motor is located at the side of the bridge and beyond the influence range of the magnet bore. A rear pedestal is omitted. The drive motor can drive the cradle supporting layer to move, and the cradle supporting layer can hook on to the intermediate cradle through a hook and drive the intermediate cradle to move. The intermediate cradle drives the upper cradle to reach into the inside of the magnet bore through its connection and driving with the upper cradle. A longer scanning range is realized by using a double-cradle structure and lowers requirement for room by removing the rear pedestal. The apparatus can ensure the free movement of the table and reduce the cradle sag during movement and ensure safety in emergencies.

The above embodiments are only used for describing the present invention in an illustrative manner, but are not intended to limit the present invention. It shall be pointed out that those skilled in the art can make improvement, modification and variation to the present invention, but these improvements, modification and variation to the present invention without departing from the spirit of the present invention should be deemed to fall within the scope of protection of the present application.

The invention claimed is:

1. An apparatus for driving and supporting cradle, the apparatus comprising:
a table base;
a cradle movable on the table base, said cradle comprising an intermediate cradle moveable relative to the table base and an upper cradle moveable relative to the intermediate cradle;
wherein the table base is coupled to the intermediate cradle using a first rack and gear structure comprising a first rack fixed on said upper cradle and a first gear fixed on said intermediate cradle, wherein the first rack is engaged with the first gear on the intermediate cradle, the first gear configured to rotate and drive the upper cradle to move using the first rack when the intermediate cradle moves, and wherein the intermediate cradle is coupled to the upper cradle using a second rack and gear structure comprising a second gear fixed on said intermediate cradle and a second rack fixed on the table base, wherein the second rack is engaged with the second gear on the intermediate cradle, a movement of the intermediate cradle drives the second gear to rotate and move relative to the table base; and
wherein the first and second gears on said intermediate cradle are located at respective first and second sides of the intermediate cradle, wherein the first and second gears each comprise a coaxial pulley, the two pulleys linked using a belt, links the two pulleys, the pulleys configured to drive the first and second gears, and wherein the first and gears and the first and second racks configured to drive the upper cradle and the intermediate cradle to move in a same direction.

2. The apparatus according to claim 1, wherein said first and second gears each have a same radius, and the two pulleys each have a same number of teeth.

3. The apparatus according to claim 1 further comprising a handle on an outer side of said intermediate cradle opposite to a direction of movement of said intermediate cradle.

4. The apparatus according to claim 1 further comprising a cradle supporting part separate from a table, said cradle supporting part configured to support a part of the cradle when the part of the cradle extends beyond the table base.

5. The apparatus according to claim 4, wherein said cradle supporting part comprises a bridge and a cradle supporting layer, said cradle supporting layer configured to move on the bridge and to provide support below the cradle.

6. The apparatus according to claim 5, further comprising:
a motor positioned at a side of said bridge; and
a gearing, wherein the motor is coupled to the gearing and the gearing is coupled to the cradle supporting layer.

7. The apparatus according to claim 6, wherein:
said gearing comprises pulleys and a belt; and
the motor is configured to drive the pulleys and the belt of the gearing, and the gearing is configured to drive the cradle supporting layer to move on the bridge.

8. The apparatus according to claim 5 further comprising:
a first hook positioned on an outer side of the intermediate cradle in a direction of movement of the intermediate cradle; and
a second hook positioned on an outer side of the cradle supporting layer, the cradle supporting layer outer side near the cradle, wherein the second hook is configured to engage the first hook when the cradle supporting layer is adjacent the intermediate cradle.

9. A magnetic resonance system comprising a table and a magnet bore, said magnetic resonance system comprising:
a table base;
a cradle moveable on the table base, the cradle comprising an intermediate cradle and an upper cradle;
a first rack and gear structure coupling the table base to the intermediate cradle, the intermediate cradle moveable relative to the table base, the first rack and gear structure comprising:
a first rack fixed on said upper cradle; and
a first gear fixed on said intermediate cradle, wherein the first rack is engaged with the first gear on the intermediate cradle, the first gear configured to rotate and drive the upper cradle to move using the first rack when the intermediate cradle moves; and
a second rack and gear structure coupling the intermediate cradle to the upper cradle, the upper cradle moveable relative to the intermediate cradle, the second rack and gear structure comprising:
a second gear fixed on said intermediate cradle; and
a second rack fixed on the table base, wherein the second rack is engaged with the second gear on the intermediate cradle, a movement of the intermediate cradle drives the second gear to rotate and move relative to the table base; and wherein the first and second gears on said intermediate cradle are located at respective first and second sides of the intermediate cradle, wherein the first and second gears each comprise a coaxial pulley, the two pulleys linked using a belt, links the two pulleys, the pulleys configured to drive the first and second gears, and wherein the first and gears and the first and second racks configured to drive the upper cradle and the intermediate cradle to move in a same direction.

10. The magnetic resonance system according to claim 9, wherein said first and second gears each have a same radius, and the two pulleys each have a same number of teeth.

11. The magnetic resonance system according to claim 9 further comprising a handle on an outer side of said intermediate cradle opposite to a direction of movement of said intermediate cradle.

12. The magnetic resonance system according to claim 9 further comprising a cradle supporting part separate from a table, said cradle supporting part configured to support a part of the cradle when the part of the cradle extends beyond the table base.

13. The magnetic resonance system according to claim 12, wherein said cradle supporting part comprises a bridge and a cradle supporting layer, said cradle supporting layer configured to move on the bridge and to provide support below the cradle.

14. The magnetic resonance system according to claim 13, further comprising:
 a motor positioned at a side of said bridge and beyond the influence range of the magnet bore; and
 a gearing, wherein the motor is coupled to the gearing and the gearing is coupled to the cradle supporting layer.

15. The magnetic resonance system according to claim 14, wherein:
 said gearing comprises pulleys and a belt; and
 the motor is configured to drive the pulleys and the belt of the gearing, and the gearing is configured to drive the cradle supporting layer to move on the bridge.

16. The magnetic resonance system according to claim 13 further comprising:
 a first hook positioned on an outer side of the intermediate cradle in a direction of movement of the intermediate cradle; and
 a second hook positioned on an outer side of the cradle supporting layer, the cradle supporting layer outer side near the cradle, wherein the second hook is configured to engage the first hook when the cradle supporting layer is adjacent the intermediate cradle.

* * * * *